United States Patent [19]
Stringfellow et al.

[11] Patent Number: 4,543,248
[45] Date of Patent: Sep. 24, 1985

[54] METHOD FOR IMMUNOREGULATION WITH 6-ARYL PYRIMIDINE COMPOUNDS

[75] Inventors: Dale A. Stringfellow; Patricia E. Fast, both of Kalamazoo, Mich.

[73] Assignee: The Upjohn Company, Kalamazoo, Mich.

[21] Appl. No.: 366,758

[22] Filed: Apr. 8, 1982

Related U.S. Application Data

[63] Continuation of Ser. No. 225,159, Jan. 15, 1981, abandoned, which is a continuation of Ser. No. 79,850, Sep. 28, 1979, abandoned, which is a continuation-in-part of Ser. No. 22,205, Mar. 19, 1979, abandoned.

[51] Int. Cl.[4] ............................................. A61K 31/505
[52] U.S. Cl. ..................................................... 514/272
[58] Field of Search ......................................... 424/251

[56] References Cited

U.S. PATENT DOCUMENTS 2,704,285  3/1955  Rorig ................................. 424/251

Primary Examiner—Jerome D. Goldberg
Attorney, Agent, or Firm—William G. Jameson; Joan Thierstein; John J. Killinger

[57] ABSTRACT

A method for altering the immunoregulatory system of humans and animals by administering a 6 aryl pyrimidine compound or a salt thereof in association with a pharmaceutical carrier.

4 Claims, No Drawings

METHOD FOR IMMUNOREGULATION WITH 6-ARYL PYRIMIDINE COMPOUNDS

CROSS REFERENCE TO RELATED APPLICATIONS

This application is a continuation of application Ser. No. 225,159, filed Jan. 15, 1981, now abandoned, which is a continuation of application Ser. No. 79,850, filed Sept. 28, 1979, now abandoned, which in turn is a continuation-in-part of application Ser. No. 22,205, filed Mar. 19, 1979, now abandoned.

BACKGROUND OF THE INVENTION

The preparation and use of 2-amino-5-halo-6-alkyl-4-pyrimidinols as antiviral agents is known (U.S. Pat. No. 3,956,302 and Nichols, Weed and Underwood, Antimicrobial Agents and Chemotherapy 9,433, 1976). Preparation of 2-amino-5-bromo-6-phenyl-4-pyrimidinol (V, where $X_3$ is Br and $X_1$ is phenyl) has been reported (Brown and Stevens, JCS Perkin I, 1023, 1975) but no utility has been described for this material. Snell, Elias and Freeman in GB Pat. No. 1,223,686 (1967) disclose a variety of 5,6-disubstituted 2-amino-4-pyrimidinols, such as 2-dimethylamino-5-bromo-6-methyl-4-pyrimidinol. Various 5-unsubstituted 2-amino-6-aryl-pyrimidinols are known (e.g., Shirahawa, Yakuyaku Fasshi 50, 1562, 1960 (CA 55, 10651b); Kulkarui et al., J. Sci. and Ind. Res. Indil. 19C, 6, 1960; and U.S. Pat. No. 2,776,283. Diuretics and cardioregulatory properties are described for various 2-amino and 2-substituted amino-5aminomethyl and 5-aryl-6-aryl-4-pyrimidinols, U.S. Pat. Nos. 2,704,285, 2,723,777 and 2,776,283.

BRIEF DESCRIPTION OF THE INVENTION

This invention relates to 6-aryl pyrimidine compounds which have been found to be useful for treatment of acquired or congenital hypogammaglobulinemia, acquired or congenital agammaglobulinemia.

DETAILED DESCRIPTION OF THE INVENTION

The compounds of this invention are prepared from β-keto ester compounds. The starting β-keto esters are prepared as follows.

A four step procedure starting with a compound of the formula Ia wherein Z is alkyl of from 1 to 5 carbon atoms, inclusive, including isomeric forms, or

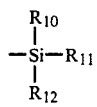

wherein $R_{10}$, $R_{11}$ and $R_{12}$ are the same or different and are alkyl of from 1 to 5 carbon atoms, inclusive, including isomeric forms or phenyl; and X and $X_1$ are as defined above.

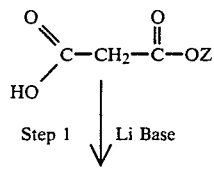

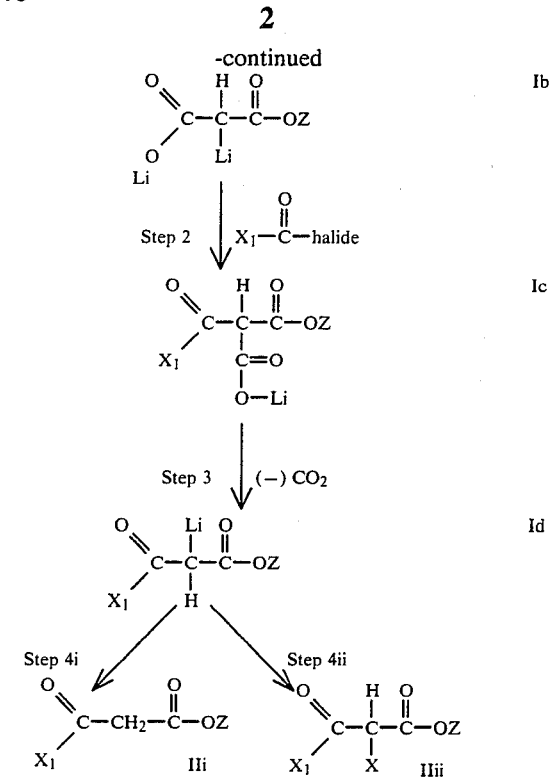

Although the reaction sequence is set forth as four steps for clarity, from the chemists point of view the reaction is "one-step" in that the sequence takes place in a single reaction vessel without requirement for separation and purification after each reaction.

In step 1 the starting material, monoalkyl malonate, preferably monoethylmalonate Ia ($Z=C_2H_5$), is treated in dry solvent with two equivalents of lithium base at reduced temperature.

Dry solvents can be, for example, tetrahydrofuran, diglyme, glyme, dioxane, hexamethylphosphoric triamide, or dimethylformamide.

By lithium base is meant for example compounds of the formula $R_8Li$ wherein $R_8$ is n-butyl, methyl, phenyl, t-butyl, s-butyl or $LiN(R_9)_2$ is isopropyl, cyclohexyl, and trimethylsilyl or a combination thereof. n-butyl lithium is preferred.

By reduced temperature is meant from 0° C. to −80° C. with a starting temperature of about −70° C. preferred.

Following the addition of the lithium base, with concommittant rise in temperature, the reaction mixture is recooled to about −65° C. whereupon an acid halide

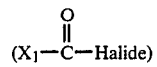

is added (Step 2). The acid halide can be added either neat or diluted with dry solvent. Dropwise addition of acid halide in dry solvent at about −65° C. is preferred.

The optimum ratio of malonate to acid halide is 1.7 (or greater) for highest yields. Acylation (step 2) and decarboxylation (step 3) to afford Id is hastened by allowing the reaction temperature to warm slowly to room temperature.

Step 4i, or work up procedure, simply involves quenching the reaction a the appropriate time with dilute acid followed by extraction with ether. The organic phase is washed with bicarbonate, dried, and concentrated to yield the desired β-ketoester, IIi.

Alternatively, in step 4ii (X is not hydrogen), at least one equivalent of X-chloride, -bromide, or -iodide (preferably X-bromide or X-iodide) is added at room temperature and the reaction mixture allowed to stand until the alkylation is complete. If desired, the mixture may be warmed to hasten the alkylation. The mixture is then quenched with dilute acid, extracted with ether and the ether phase washed and concentrated, as described for step 4i, to yield the desired α-substituted β-keto ester, IIii. If desired, IIii may be further purified by conventional methods such as cyromatography, distillation, and the like.

EXAMPLES

EXAMPLE 1

Ethylisobutryl Acetate

To a 1 liter, 3-necked round-bottom flask, fitted with a nitrogen inlet thermometer, and an overhead stirrer is added 19.8 g. (147 mM) of monoethylmalonate, 350 ml. of dried THF and 2 mg. of bipyridyl. The solution is cooled to −70° C. and a 1.6 M solution of n-butyllithium in hexane (Foote Chemicals Co. or Aldrich Chemical Co.) is added, dropwise at −70° C. to −5° C. until a pink color persisted. The temperature is allowed to slowly rise to −5° C., throughout the butyllithium addition, during which time and pink color formed will dissipate. After the pink color remains for five minutes at −5° C. (approx. 210 ml. of butyllithium has been added), the mixture is cooled to −65° C. and 7.9 ml. (7.98 g. 75 mM) of isobutyryl choride is added dropwise at −60° C. to −65° C. The solution is stirred vigorously at −60° C. to −65° C., for 5 minutes and poured into 500 ml. of ether+300 ml. of ice-cold 1 N nydrochloric acid. After shaking, the layers are separated and the organic layer is washed 2×150 ml. saturated aqueous sodium bicarbonate 1×150 ml. water and dried over sodium sulfate (anhyd.). The etheral solution is filtered, the solids washed with ether and the combined filtrates evaporated to dryness to yield 11.7 g. (98.4%) of ethylisobutyryl acetate, m.w. 158.19.

NMR (CDCl$_3$):δ 4.38-4 (q, 2H, O—CH$_2$—CH$_3$), 3.5

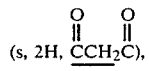
(s, 2H, CCH$_2$C), 2.96-2.41 (m, 1H, CH(CH$_3$)$_2$, 1.46-1 (m, 9H, CH$_3$).
GLPC R.T.=3.2 min (T=90° , 3′, 3% OV 17)
GC/MS M+m/e 159 (27%), 116 (100%).

EXAMPLE 2

Ethyl-n-butyryl Acetate

Following the procedure for the preparation of ethylisobutyryl acetate but substituting 7.98 g. (75 mM) of n-butyryl chloride in 50 ml. of dried THF for the 7.9 ml. of isobutyryl chloride, 11.4 g. (96.6%) of ethyl n-butyryl acetate is isolated, m.w. 158.19.

NMR (CDCl$_3$):δ 4.38-4.0 (q, 2H, OCHhd 2), 3.43 (s, 2H, COCH$_2$CO), 2.65-2.41

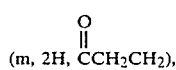
(m, 2H, CCH$_2$CH$_2$), 1-91-0.78 (m, 10H, CH$_3$CH$_2$CH$_2$C, CH$_3$ CH$_2$O) GLPC R.T.=3.1 min (T=90°, 3′, 3% OV 17).

EXAMPLE 3

Ethylpropionyl Acetate

Following the procedure for the preparation of ethylisobutyryl acetate but substituting 71. g. of monoethylmalonate (0.613 M), 1300 ml. of the THF and 28.1 g. of propionyl chloride (0.305 M) in 300 ml. THF (added dropwise) to yield 42.0 g. (95.2%) of ethylpropionyl acetate as an oil, m.w. 144.17.

NMR (CDCl$_3$):δ 4.36-4 (q, 2H, O—CH$_2$—CH$_3$), 3.41

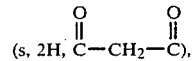
(s, 2H, C—CH$_2$—C), 2.75-2.38 (q, 2H, COCH$_2$), 1.5-0.86 (m, 5H, CH$_3$).
GLPC R. T.=5.6 min (90°, 6′, 3% OV 17.
GC/MS M+m/e (76.5%), 115 (100%).

EXAMPLE 4

Ethylphenylacetyl Acetate

Following the procedure for the preparation of ethylisobutyryl acetate but substituting 10.0 ml. (11.69 g. 75 mM) of phenylacetylchloride (Aldrich Chem. Co.) for the 7.9 ml. of isobutyryl chloride gave 15.4 g (98.8%) of ethyl phenylacetyl acetate, m.w. 206.23.

NMR (CDCl$_3$):δ 7.38-7.13 (m, 5H, Ar), 4.31-3.95 (q, 2H, OCH$_2$), 3.78 (s, 2H, CH$_2$), 3.38

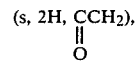
(s, 2H, CCH$_2$), 1.33-1.11 (t, 3H, CH$_3$).

EXAMPLE 5

Ethylbenzoyl Acetate

Following the procedure for the preparation of ethylisobutyryl acetate but substituting 6.06 g. of monoethylmalonate (45 mM), 250 ml. THF and 2.64 ml. of benzoylchloride (3.15 g.≈2.55 mM) and stirring the reaction mixture at −65° for 60 minutes gave 4.18 g. (97%) of ethybenzoyl acetate as an oil, m.w. 192.21. This material was isolated as a mixture of tautomers (H′—NMR).

NMR (CDCl$_3$):δ 8.06-7.25 (m, 5H, Ar), 5.66

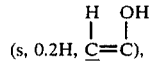
(s, 0.2H, C=C), 4.43-3.96 (m, 3.9H, OCH$_2$CH$_3$, COCH$_2$CO), 1.45-1.11 (m, 3H, CH$_3$).
GLPC R. T.=3.1 min (85°, 60 cm, UCW-98-2).
GC/MS M+m/e 192 (6.8%), 105 (100%).

EXAMPLE 6

Ethyltoluoyl Acetate

Following the procedure for the preparation of ethyl benzoyl aceatate but substituting 15.5 g. of monoethylmalonate (115 mM), 500 ml. THF and 11.1 g. (71.8 mM) of toluoyl chloride gave 13.44 g. (90.8%) of ethyl toluoyl acetate as an oil. H′-NMR indicates the desired product is a mixture of tautomers, m.w. 206.23.

NMR (CDCl$_3$):δ 8.05-7.61 (m, 2H, 2.6-ArH), 7.41-7.13 (m, 2H, 3,5-ArH) 5.63

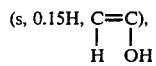

4.41-4.03 (m, 2H, CH$_2$CH$_3$), 3.95

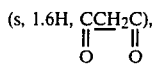

2.4 (s, 3H, ArCH$_3$), 1.43-1.11 (m, 3H, CH$_2$CH$_3$).

EXAMPLE 7

Ethylanisoyl Acetate

Following the procedure for the preparation of ethyl-benzoyl acetate but substituting 15.5 g of monoethyl malonate (115 mM), 400 ml. of THF and 12.24 G. (71.8 mM) of anisoyl chloride gave 14.45 g. (90.3%) of ethylanisoyl acetate as an oil, m.w. 222.23.

NMR (CDCl$_3$):δ 8.03-7.86 (m, 2H, 2,6-ArH), 7.08-6.86 (m, 2H, 3,5-ArH), 4.38-3.85 (m, 7H, OCH$_3$, COCH$_2$CO, OCH$_2$CH$_3$), 1.36-1.13 (t, 3H, CH$_2$CH$_3$).

EXAMPLE 8

Ethyl-p-Chlorobenzoyl Acetate

Following the procedure for the preparation of ethyl-benzoyl acetate but substituting 15.5 g. of monoethyl-malonate (115 mM), 400 ml. THF and 12.5 g. (71.5 mM) of p-chlorobenzoyl chloride gave 15.56 g. (95.6%) of ethyl p-chlorobenzoyl acetate as a solid. Recrystallization o an analytical sample from methanol gave solid ethyl-p-chlorobenzoyl acetate as a mixture of tautomers, m.w. 226.65.

NMR (CDCl$_3$):δ 7.95-7.21 (m, 4H-ArH), 5.61

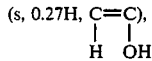

4.41-4 (m, 2H, CH$_2$CH$_3$), 3.9 (s, 1.36H, COCH$_2$CO), 1.43-1.1 (m, 3H, CH$_2$CH$_3$).

Analysis: Cal'd. for C$_{11}$H$_{11}$ClO$_3$: C, 58.28; H, 4.89; Cl, 15.64. Found: C, 58.34; H, 5.13; Cl, 15.32.

EXAMPLE 9

Ethyl 3,4-Dichlorobenzoyl Acetate

Following the procedure for the preparation of ethyl benzoyl acetate but substituting 15.5 g. (115mM) of monoethylmalonate, 400 ml. of THF, and 12.0 g. (57.5 mM) 3,4-dichlorobenzoyl chloride gave 14.56 g. (97%) of ethyl 3,4-dichlorobenzoyl acetate. This material slowly crystallized on standing at −12° C. was isolated as a mixture of tautomers, m.w. 261.1.

NMR (CDCl$_3$):δ 8.06-7.5 (m, 3H, ArH), 5.63

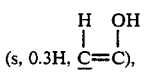

4.4-4.03 (m, 2H, CH$_2$CH$_3$), 3.93 (s, 1.42H, COCH$_2$CO), 1.46-1.13 (m, 3H, CH$_2$CH$_3$).

Analysis: Calc'd for C$_{11}$H$_{10}$Cl$_2$O$_3$: C, 50.59; H, 3.86. Found: C, 50.21, H, 4.79.

EXAMPLE 10

Ethyl-α-ethyl-benzoylacetate

To 13.2 g. of monoethylmalonate was added 300 ml. THF and 5 mg. of bipyridyl. Butyl lithium was added at −70° C. to −10° C. until a pink color persisted. The reaction mixture was recooled to −70° C. and 6.4 ml. of benzoyl chloride (0.06 M) was added. After stirring at −60° C. for 60 minutes, 28.2 g. (0.182 M) of ethyl iodide was added and the reaction mixture allowed to stir, at ambient temperature, for 18 hours. The mixture was then warmed to 50° C. and kept at 50° C. for 90 hours. At this time the entire mixture was poured into 500 ml. diethyl ether+300 ml. 1N hydrochloric acid, the layers separated, and the organic layer washed one time IN hydrochloric acid, once in saturated aqueous sodium bicarbonate and once with water. Drying over sodium sulfate (anhyd.), filtering and evaporating yielded 13.6 g. of ethyl α-ethyl-benzoylacetate as an oil.

NMR: 8.11-7.91 (m, 2H, φ), 7.66-7.30 (m, 3H, φ), 4.35-3.96 (m, 3H, COCHCO,OCH$_2$CH$_3$), 2.30-1.80 (m, 2H, CH$_2$CH$_3$), 1.43-0.76 (m, 6H, CH$_3$).

The novel compounds of this invention are represented by the formula:

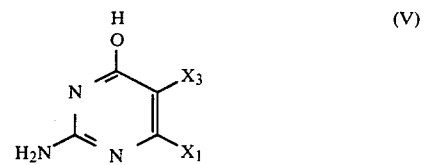

The compounds can exist in tautomer form and can be depicted as follows:

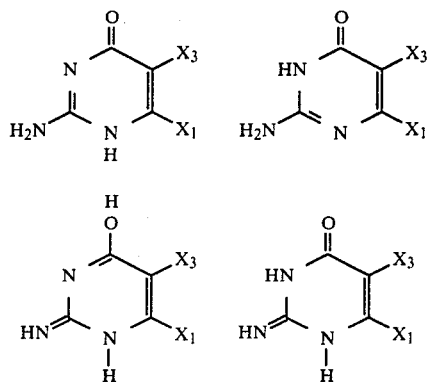

Thus they can be named as pyrimidinols or pyrimidinols or pyrimidinones.

The pyrimidine compounds can also be named as isocytosines, e.g., 2-amino-5-bromo-6m-fluorophenyl-4-pyrimidinol can also be named 5-bromo-6-m-fluorophenyl isocytosine.

The novel pyrimidines (V) can be prepared according to the following manner from the previously described βketo esters:

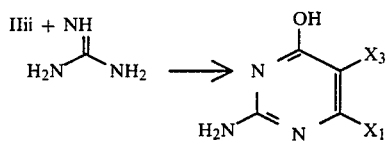

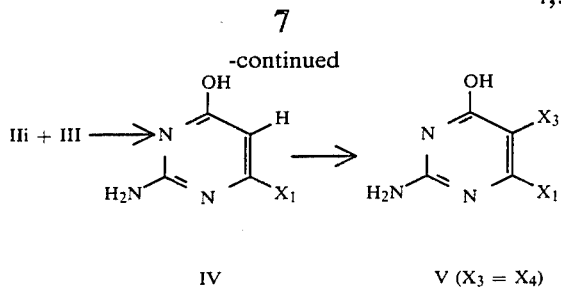

IIi + III ⟶

IV    V ($X_3 = X_4$)

The condensation of the appropriate β-keto ester IIii with guanidine (III) can be carried out in polar solvents such as ethanol, isopropanol, 1-butanol, dimethylformamide (DMF), and the like, with ethanol preferred, in the presence of a base such as a carbonate (for example, sodium carbonate or guanidium carbonat itself) or an alkoxide (such as sodium ethoxide) and the like, under reflux in the usual manner. The product V (wherein $X_3$ is $X_1$ or $X_5$) is isolated by neutralization with acid or carbon dioxide of the reaction mixture after condensation is complete as determined by TLC, and filtration orchromatography in the conventional manner.

The preparation of V (wherein $X_3$ is $X_4$) is carried out from an appropriate β-keto ester IIii and guanidine (III) as described above to yield IV in like manner. Subsequent halogenation of IV for example by treatment with N-chlorosuccinimide in acetic acid to yield V wherein $X_3=X_4=Cl$, or for example by treatment with bromine in acetic acid to yield V wherein $X_3=X_4=Br$, or for example by treatment with an equivalent of 1 N sodium hydroxide followed by iodine in cloroform to yield V wherein $X_3=X_4=I$, can be carried out to afford the novel pyrimidines V wherein $X_3=X_4$. Alternative methods of halogenation are illustrated in the following procedures. The final pyrimidines can be isolated by concentration in vacuo and aqueous trituration of the residue followed by filtration of the resultant solid.

EXAMPLE 11

General procedure and preparation of pyrimidines of the formula:

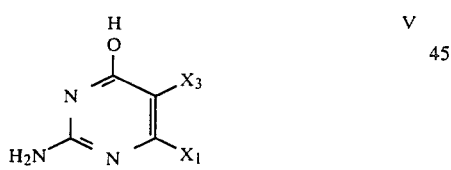

V

The compounds prepared and the procedure used are shown in Table 1.

Procedure 1

Condensation to IV or V ($X_3=X$ or $X_5$)

To 20 mM of powdered quanidine carbonate was added, under nitrogen, 120 ml. of absolute ethanol and 20 ml. of toluene. The reaction mixture was heated to reflux and 50 ml. of solvent was distilled off. The mixture was cooled to 45° C. and 40 mM of β-ketoester (II or IIii) added. This mixture was heated to reflux, with stirring, until the reaction appeared complete by TLC. Water (50 ml.) was added and the refluxing continued for an additional 30 minutes, at which time the reaction mixture was cooled to 20° C. and neutralized by addition of dry carbon dioxide or 1N aqueous hydrochloric acid. The mixture was allowed to cool at 5° C. for 18 hours, filtered and the resulting precipitate washed well with water followed by diethyl ether. The solids were dried at 60° C. under vacuum to yield the desired pyrimidine as a white solid. If the crude solids were not analytically pure they could be recrystallized from appropriate solvents, such as aqueous DMF, aqueous ethanol, and the like.

Procedure 2 condensation

The reaction was carried out exactly as described in Procedure 1, except, after neutralization (addition of carbon dioxide or 1N hydrochloric acid) the aqueous mixture was evaporated to dryness under vacuum and 100 ml. of water and 100 ml. ethyl ether were added. The mixture was shaken and allowed to sit at 5° C. for 18 hours. The mixture was filtered and solids washed well with water followed by ethyl ether. Drying and crystallization as described in Procedure 1 gave analytically pure pyrimidine.

Procedure 3

Bromination (wherein $X_3=Br$)

To 15 mM of the appropriate pyrimidine was added 80 ml. of glacial acetic acid. The reaction mixture was warmed to 50° C. to affect solution (if solids were in solution at 22° C., then it was not necessary to warm) and 0.81 ml. of $Br_2$ was added. The solution was allowed to stir at ambient temperature for 3 hours. The reaction was evaporated to dryness, under vacuum, and, to the resulting solids was added 150 ml. of hot water. The slurry was heated to reflux and allowed to cool to 22° C.

The solids were filtered and washed well with water. The solids were pulverized and reheated with 150 ml. of water as described previously. This procedure was repeated. The pyrimidine was dried in a vacuum oven at 60° C. to give analytically pure material. If desired, it can be recrystallized from water:DMF by adding DMF slowly to a stirring slurry of compound in 150 ml. of boiling water until solution occurs. Cooling and filtering yielded analytically pure material.

Procedure 4

Bromination (wherein $X_3=Br$)

To 15 mM of the appropriate pyrimidine was added 50 ml. of water and 0.66 g. of NaOH (16.5 mM). The solution was allowed to stir at ambient temperature for 30 minutes and 0.9 ml. of $Br_2$ (22.62 g. 16.5 mM) in 50 ml. of chloroform was added. The reaction mixture was stirred, vigorously, for 2 hours and filtered. Solids were washed well with water, followed by water and dried at 60° C. in a vacuum oven for 18 hours. Recrystallization from water:DMF as per Procedure 3 gave analytically pure material.

Procedure 5

Iodination (wherein $X_3=I$)

To 15 mM of the appropriate pyrimidine was added 50 ml. of water and 0.80 g. (20 mM) of sodium hydroxide. The mixture was stirred and heated to 50° C. until solution occurred. A slurry of 3.79 g. of powdered $I_2$ (15 mM) in 100 ml. of chloroform was added. The excess $I_2$ was washed into the reaction vessel with an additional 30 ml. of chloroform. The mixture was allowed to stir, vigorously, at ambient temperature for four hours.

The solids were filtered, washed well with water (until water was neutral to pH paper) followed by either acetone or ethyl acetate until the organic wash was colorless. It is often desirable to pulverize the solids before washing. The solids were dried at 60° C. in a vacuum oven. If material is not analytically pure it may be recrystallized from water:DMF by adding DMF slowly to a vigorously stirring slurry of the pyrimidine in 150 ml. of boiling water until solution occures. Cooling, filtering and drying at 60° C. gives analytically pure material.

Procedure 6

Iodination ($X_3 = I$)

To 1.95 mM of the appropriate pyrimidine was added 25.0 ml. of glacial acetic acid and 434 mg. (2 mM) of N-iodosuccinimide. The reaction mixture was allowed to stir at ambient temperature for 5 days. The mixture was evaporated to dryness under vacuum at 50° C. The solids were purified by heating with 50 ml. of absolute ethanol at reflux and cooling to room temperature. Filtering and washing with absolute ethanol gave the pure 5-iodopyrimidine.

Procedure 7

Chlorination ($X_3 = Cl$)

To 0.1 M of a 6-arylpyrimidine was added 500 ml. of glacial acetic acid and 14.6 g. of N-chlorosuccinimide (0.11 M). The reaction mixture was heated on a steam bath for 1½ hours. The reaction mixture was cooled to 22° C., evaporated to a volume of 200 ml. and filtered. The solids thus obtained were washed with glacial acetic cid followed by ethyl ether and dried at 60° C. in a vacuum oven. If the solids are not analytically pure, they can be recrystallized from water:DMF by adding DMF to a boiling slurry of the pyrimidine in 500 ml. water until solution occurred. Cooling and filtering gives an analytically pure 5-chloro-6-arylpyrimidine.

Procedure 8

Fluorination ($X_3 = F$)

The introduction of fluorine into the 5-position of the pyrimidine ring is effected by fluorination of IV with trifluoromethylhypofluorite followed by base according to the procedure of M. J. Robbins and S. R. Naik, J. Am. Chem. Soc. 93, 5277 (1971). Alternatively, if desired, IV may be fluorinated directly with fluorine-pyridine complex to produce V where $X_3 = F$ by the procedure described by H. Meinert and D. Cech, Z. Chem. 12, 292 (1972).

Procedure 9

Preparation of V ($X_3 = CF_3$)

Preparation of V wherein $X_3 = CF_3$ may be achieved starting with V wherein $X_3 = I$ by the exchange procedures described by D. Cech, R. Wohlfeil and G. Efzold, Nucleic Acids Research 2, 2183 (1975) and by Y. Kobayashi, I. Kumadaki and F. Yamamato J.C.S. Chem. Comm. 536 (1977) using trifluoromethyliodide and copper-bronze. In like manner, 5-perfluoroalkyl-pyrimidines (V, $X_3$ = perfluoroalkyl) may be prepared using perfluoroalkyl iodides.

Alternatively, if desired, the trifluoromethyl or perfluoroalkyl group can be introduced earlier at the β-ketoester stage and the resulting trifluoromethyl or perfluoroalkyl β-ketoester ccondensed with guanidine as in Procedures 1 or 2 to produce V ($X_3 = CF_3$ or perfluoroalkyl). Preparation of a trifluoromethyl or perfluoromethyl, β-ketoester may be achieved by methods known in the art. For example, condensation of

and $CH_2\text{-}CH_2$ in the presence of $SbF_5$ affords

and carboalkoxylation under standard conditions yields

procedure 10

Preparation of V ($X_3 = CH_2 - X_4$)

Preparation of V wherein $X_3 = CH_2X_4$ can be accomplished under standard conditions known in the art from the corresponding hydroxymethyl (V, wherein $X_3$32 $CH_2OH$) intermediates. These intermediates can be prepared under standard conditions from IV and formaldehyde or alternatively from a suitably protected β-ketoester, for example $ArCOCH(CH_2OCH_2\phi)CO_2E_t$, itself prepared from I by the previously described chemistry wherein X is $-CH_2OCH_2\phi$. Hydrogenylitic or protolytic removal of the benzyl group will yield V wherein $X_3 = CH_2OH$, after condensation of the β-ketoester with guanidine as described in Procedure 1. The resulting 5-hydroxymethylpyrimidine is transformed into the corresponding 5-halomethylpyrimidine by standard procedures known in the art, either via displacement reactions on the corresponding 5-tosyloxymethyl derivative (formed with toluensulfonyl chloride in pyridine) with alkali or alkaline earth halogen salts, or directly with the known phosphine - carbon tetrahalide methodology.

| $X_0$ | $X_1$ | Procedure No.[a] | | C | H | N | F | Cl | Br | I |
|---|---|---|---|---|---|---|---|---|---|---|
| Cl | φ | 7 | CALCULATED | 54.19 | 3.63 | 18.95 | | 15.99 | | |
| | | | FOUND - m.p., other[b] | 54.64 | 3.75 | 19.15 | | 15.38 | | |
| Br | φ | 3 | CALCULATED | 45.13 | 3.03 | 15.79 | | | 30.03 | |
| | | | FOUND - m.p., other[b] | 45.20 | 3.00 | 15.66 | | | 29.92 | |
| I | φ | 5 | CALCULATED | 38.36 | 2.57 | 13.42 | | | | 40.53 |
| | | | FOUND - m.p., other[b] | 38.46 | 2.57 | 13.28 | | | | 39.74 |
| $CH_3$ | φ | 1 | CALCULATED | 65.65 | 5.51 | 20.88 | | | | |
| | | | FOUND | 65.52 | 5.38 | 20.86 | | | | |

-continued

| $X_0$ | $X_1$ | Procedure No.[a] | | C | H | N | F | Cl | Br | I |
|---|---|---|---|---|---|---|---|---|---|---|
| | | | m.p., other[b] | | | | | | | |
| $CH_3CH_2$ | φ | 1 | CALCULATED | 66.95 | 6.08 | 19.52 | | | | |
| | | | FOUND - | 66.63 | 5.94 | 19.63 | | | | |
| | | | m.p., other[b] | | | | | | | |
| Br | 4-$CH_3$ φ.HBr | 3 | CALCULATED | 36.59 | 2.79 | 11.63 | | | 44.27 | |
| | | | FOUND - | 37.48 | 3.18 | 12.01 | | | 43.36 | |
| | | | m.p., other[b] | | | | | | | |
| I | 4-$CH_3$ φ | 5 | CALCULATED | 40.38 | 3.08 | 12.84 | | | | 38.80 |
| | | | FOUND - | 40.32 | 3.19 | 12.93 | | | | 38.14 |
| | | | m.p., other[b] | | | | | | | |
| Br | 4-Cl φ | 3 | CALCULATED | 39.96 | 2.34 | 13.98 | | 11.79 | 26.59 | |
| | | | FOUND | 39.92 | 2.38 | 14.12 | | 10.65 | 27.87 | |
| | | | m.p., other[b] | | | | | | | |
| Cl | 3-F φ | 7 | CALCULATED | 50.12 | 2.95 | 17.53 | 7.93 | 14.80 | | |
| | | | FOUND - | 50.16 | 2.90 | 17.43 | 7.84 | 14.40 | | |
| | | | m.p., other[b] | | | | | | | |
| Br | 3-F φ | 3 | CALCULATED | 42.27 | 2.48 | 14.79 | 6.68 | | 28.13 | |
| | | | FOUND - | 42.24 | 2.47 | 14.73 | 6.74 | | 28.15 | |
| | | | m.p., other[b] | | | | | | | |
| I | 3-F φ | 5 | CALCULATED | 36.27 | 2.13 | 12.64 | 5.74 | | | 38.73 |
| | | | FOUND - | 36.30 | 2.18 | 12.65 | 5.59 | | | 38.10 |
| | | | m.p., other[b] | | | | | | | |
| Br | 3-Br φ | 3 | CALCULATED | 34.81 | 2.04 | 12.18 | | | 46.32 | |
| | | | FOUND - | 34.78 | 1.78 | 12.15 | | | 45.72 | |
| | | | m.p., other[b] | | | | | | | |
| I | 3-Br φ | 5 | CALCULATED | 30.64 | 1.80 | 10.72 | | | 20.38 | 32.07 |
| | | | FOUND - | 30.95 | 1.89 | 11.05 | | | 20.54 | 32.06 |
| | | | m.p., other[b] | | | | | | | |
| Cl | 3-I φ | 7 | CALCULATED | 34.56 | 2.03 | 12.09 | | 10.20 | | 36.51 |
| | | | FOUND - | 34.55 | 1.94 | 11.77 | | 10.54 | | 36.2 |
| | | | m.p., other[b] | | | | | | | |
| Br | 3-I φ | 3 | CALCULATED | 30.64 | 1.80 | 10.72 | | | 20.39 | 32.37 |
| | | | FOUND - | 30.86 | 1.94 | 10.90 | | | 20.10 | 32.08 |
| | | | m.p., other[b] | | | | | | | |
| I | 3-I φ | 5 | CALCULATED | 27.33 | 1.60 | 9.57 | | | | 57.82 |
| | | | FOUND - | 27.58 | 1.77 | 9.62 | | | | 56.22 |
| | | | m.p., other[b] | | | | | | | |
| Cl | 3-$CH_3O$ φ | 7 | CALCULATED | 52.58 | 3.98 | 16.73 | | 13.94 | | |
| | | | FOUND - | 52.22 | 3.95 | 16.65 | | 13.91 | | |
| | | | m.p., other[b] | | | | | | | |
| Br | 3-$CH_3O$ φ | 3 | CALCULATED | 44.59 | 3.40 | 14.19 | | | 26.99 | |
| | | | FOUND - | 44.22 | 3.62 | 14.11 | | | 26.59 | |
| | | | m.p., other[b] | | | | | | | |
| I | 3-$CH_3O$ φ | 5 | CALCULATED | 38.51 | 2.94 | 12.25 | | | | 36.98 |
| | | | FOUND - | 38.78 | 3.03 | 12.16 | | | | 36.85 |
| | | | m.p., other[b] | | | | | | | |
| Br | 3-$NO_2$ φ | 3 | CALCULATED | 38.61 | 2.27 | 18.01 | | | 25.68 | |
| | | | FOUND - | 38.71 | 2.23 | 18.23 | | | 25.75 | |
| | | | m.p., other[b] | | | | | | | |
| I | 3-$NO_2$ φ | 5 | CALCULATED | 33.54 | 1.97 | 15.65 | | | | 35.44 |
| | | | FOUND - | 31.97 | 1.91 | 14.96 | | | | 32.57 |
| | | | m.p., other[b] | | | | | | | |
| Br | 3-$CF_3$ φ | 3 | CALCULATED | 39.54 | 2.11 | 12.57 | 17.06 | | 23.92 | |
| | | | FOUND - | 39.79 | 2.02 | 12.80 | 17.04 | | 24.11 | |
| | | | m.p., other[b] | | | | | | | |
| I | 3-$CF_3$ φ | 5 | CALCULATED | 34.66 | 1.85 | 11.02 | 14.95 | | | 33.30 |
| | | | FOUND - | 34.65 | 1.47 | 11.22 | 14.87 | | | 33.39 |
| | | | m.p., other[b] | | | | | | | |
| H | αnaphthyl | 1 | CALCULATED | 70.87 | 4.67 | 17.71 | | | | |
| | | | FOUND - | 70.76 | 4.76 | 17.49 | | | | |
| | | | m.p., other[b] | | | | | | | |
| Br | αnaphthyl | 3 | CALCULATED | 53.18 | 3.19 | 13.29 | | | 25.27 | |
| | | | FOUND - | 53.05 | 3.24 | 12.71 | | | 25.23 | |
| | | | m.p., other[b] | | | | | | | |
| | | | FOUND - | 45.53 | 2.87 | 19.56 | | 17.33 | | |
| | | | m.p., other[b] | | | | | | | |
| Br | 2-furyl | 4 | CALCULATED | 37.52 | 2.35 | 16.41 | | | 31.20 | |
| | | | FOUND - | 36.66 | 2.41 | 16.10 | | | 32.39 | |
| | | | m.p., other[b] | | | | | | | |
| I | 2-furyl | 5 | CALCULATED | 31.70 | 2.00 | 13.87 | | | | |
| | | | FOUND - | 33.10 | 1.94 | 14.40 | | | | |
| | | | m.p., other[b] | | | | | | | |
| I | α-naphthyl | 5 | CALCULATED | 46.30 | 2.77 | 11.57 | | | | 34.95 |
| | | | FOUND - | 46.54 | 2.90 | 11.41 | | | | 34.86 |
| | | | m.p., other[b] | | | | | | | |
| $CH_3$ | α-naphthyl | 1 | CALCULATED | 71.69 | 5.21 | 16.72 | | | | |
| | | | FOUND - | 70.91 | 5.34 | 16.75 | | | | |
| | | | m.p., other[b] | | | | | | | |
| Cl | 2-furyl | 7 | CALCULATED | 45.40 | 2.85 | 19.86 | | 16.75 | | |

-continued

| $X_0$ | $X_1$ | Proce-dure No.[a] | | C | H | N | F | Cl | Br | I |
|---|---|---|---|---|---|---|---|---|---|---|
| I | 4-Cl φ | 5 | CALCULATED | 34.56 | 2.03 | 12.09 | | 10.20 | | 36.52 |
| | | | FOUND - | 35.00 | 2.29 | 12.46 | | 10.64 | | 35.02 |
| | | | m.p., other[b] | | | | | | | |
| Br | 3,4-Cl₂φ.HBr | 3 | CALCULATED | 28.87 | 1.45 | 10.10 | | 17.05 | 38.43 | |
| | | | FOUND - | 29.68 | 1.77 | 10.86 | | 16.64 | 38.28 | |
| | | | m.p., other[b] | | | | | | | |
| I | 3,4-Cl₂ φ | 5 | CALCULATED | 31.44 | 1.58 | 11.00 | | 18.56 | | 33.22 |
| | | | FOUND - | 31.27 | 1.65 | 10.99 | | 17.07 | | 35.43 |
| | | | m.p., other[b] | | | | | | | |
| Br | 3,5-Cl₂ φ | 3 | CALCULATED | 35.85 | 1.80 | 12.54 | | 21.17 | 23.85 | |
| | | | FOUND - | 36.07 | 1.82 | 12.69 | | 20.18 | 25.85 | |
| | | | m.p., other[b] | | | | | | | |
| I | 3,5-Cl₂ φ | 5 | CALCULATED | 31.44 | 1.58 | 11.00 | | 18.56 | | 33.22 |
| | | | FOUND - | 31.12 | 1.50 | 10.75 | | 19.20 | | 28.11 |
| | | | m.p., other[b] | | | | | | | |
| Cl | 2,5-Cl₂ φ | 7 | CALCULATED | 41.33 | 2.08 | 14.46 | | 36.61 | | |
| | | | FOUND - | | | | | | | |
| | | | m.p., other[b] - 260-280d | 41.54 | 2.18 | 14.63 | | 36.50 | | |
| Br | 2,5-Cl₂ φ | 3 | CALCULATED | | | | | | | |
| | | | FOUND - | | | | | | | |
| | | | m.p., other[b] - 255-275d | | | | | | | |
| I | 2,5-Cl₂ φ | 5 | CALCULATED | 31.44 | 1.58 | 11.00 | | | | |
| | | | FOUND - | | | | | | | |
| | | | m.p., other[b] - 180-181 | 31.54 | 1.62 | 10.98 | | | | |
| Cl | 3-Cl φ | 7 | CALCULATED | 46.90 | 2.75 | 16.41 | | 27.69 | | |
| | | | FOUND - | 46.95 | 2.67 | 16.54 | | 27.91 | | |
| | | | m.p., other[b] | | | | | | | |
| Br | 3-Cl φ | 3 | CALCULATED | 39.96 | 2.34 | 13.98 | | 11.79 | 16.59 | |
| | | | FOUND - | 40.33 | 2.40 | 14.00 | | 11.62 | 26.99 | |
| | | | m.p., other[b] | | | | | | | |
| I | 3-Cl φ | 5 | CALCULATED | 34.56 | 2.03 | 12.09 | | 10.20 | | 36.52 |
| | | | FOUND - | 34.80 | 2.12 | 12.12 | | 9.93 | | 36.46 |
| | | | m.p., other[b] | | | | | | | |
| Br | 2-pyridyl.HBr | 3 | CALCULATED | 31.06 | 2.32 | 16.10 | | | 45.93 | |
| | | | FOUND - | 30.47 | 3.00 | 16.09 | | | 45.54 | |
| | | | m.p., other[b] | | | | | | | |
| I | 2-pyridyl | 5 | CALCULATED | 34.41 | 2.25 | 17.84 | | | | 40.40 |
| | | | FOUND - | 34.39 | 2.39 | 18.06 | | | | 40.25 |
| | | | m.p., other[b] | | | | | | | |
| Br | 3-pyridyl | 3 | CALCULATED | 40.47 | 2.64 | 20.99 | | | | |
| | | | FOUND - | 39.89 | 2.66 | 21.85 | | | | |
| | | | m.p., other[b] | | | | | | | |
| I | 3-pyridyl | 5 | CALCULATED | 34.41 | 2.24 | 17.84 | | | | 40.40 |
| | | | FOUND - | 34.83 | 2.22 | 18.23 | | | | 40.47 |
| | | | m.p., other[b] | | | | | | | |
| Cl | 2-Cl φ | 7 | CALCULATED | 46.90 | 2.75 | 16.41 | | 27.69 | | |
| | | | FOUND - | 46.75 | 2.74 | 16.23 | | 27.64 | | |
| | | | m.p., other[b] | | | | | | | |
| Br | 2-Cl φ | 3 | CALCULATED | 40.00 | 2.35 | 13.98 | | 11.80 | 26.69 | |
| | | | FOUND - | 49.90 | 2.29 | 14.10 | | 11.05 | 28.07 | |
| | | | m.p., other[b] | | | | | | | |
| I | 2-Cl φ | 5 | CALCULATED | 34.56 | 2.03 | 12.09 | | 10.20 | | 35.52 |
| | | | FOUND - | 34.36 | 2.09 | 12.16 | | 10.75 | | 34.75 |
| | | | m.p., other[b] | | | | | | | |
| Cl | 2-CH₃ φ | 7 | CALCULATED | 56.05 | 4.27 | 17.83 | | | 15.04 | |
| | | | FOUND - | 55.95 | 4.03 | 17.64 | | | 15.01 | |
| | | | m.p., other[b] | | | | | | | |
| Br | 2-CH₃ φ | 3 | CALCULATED | 47.16 | 3.59 | 15.00 | | | 28.64 | |
| | | | FOUND - | 47.04 | 3.77 | 14.81 | | | 29.09 | |
| | | | m.p., other[b] | | | | | | | |
| I | 2-CH₃ φ | 5 | CALCULATED | 40.38 | 3.08 | 12.84 | | | | 38.79 |
| | | | FOUND - | 40.10 | 3.04 | 12.73 | | | | 39.05 |
| | | | m.p., other[b] | | | | | | | |
| Cl | 2-CH₃O φ | 7 | CALCULATED | 52.49 | 4.01 | 16.70 | | | 14.09 | |
| | | | FOUND - | 52.56 | 4.27 | 16.69 | | | 13.11 | |
| | | | m.p., other[b] | | | | | | | |
| Br | 2-CH₃O φ | 3 | CALCULATED | 44.61 | 3.40 | 14.19 | | | 26.99 | |
| | | | FOUND - | 44.91 | 3.38 | 14.39 | | | 26.64 | |
| | | | m.p., other[b] - 288-289 | | | | | | | |
| Br | 2-F φ | 3 | CALCULATED | 42.27 | 2.48 | 14.79 | | | | |
| | | | FOUND - | 42.86 | 2.76 | 14.47 | | | | |
| | | | m.p., other[b] | | | | | | | |
| I | 2- F φ | 5 | CALCULATED | 36.27 | 2.13 | 12.69 | 5.73 | | | 38.33 |
| | | | FOUND - | 36.54 | 2.14 | 12.83 | 5.65 | | | 38.04 |
| | | | m.p., other[b] | | | | | | | |
| Cl | 2-F φ | 7 | CALCULATED | 50.12 | 1.94 | 17.52 | | 14.79 | | |
| | | | FOUND - | 49.82 | 3.00 | 17.13 | | 14.38 | | |
| | | | m.p., other[b] | | | | | | | |
| I | 4-F φ | 5 | CALCULATED | 36.27 | 2.13 | 12.69 | 5.73 | | | 38.33 |

-continued

| $X_0$ | $X_1$ | Procedure No.[a] | | C | H | N | F | Cl | Br | I |
|---|---|---|---|---|---|---|---|---|---|---|
| | | | FOUND - m.p., other[b] | 36.11 | 2.15 | 12.53 | 5.63 | | | 38.03 |
| Br | 4-F φ | 3 | CALCULATED | 42.47 | 2.48 | 14.79 | 6.68 | | | |
| | | | FOUND - m.p., other[b] | 41.81 | 2.53 | 14.47 | 6.43 | | | |
| Cl | 4-F φ | 7 | CALCULATED | 50.12 | 2.94 | 17.53 | | 14.79 | | |
| | | | FOUND - m.p., other[b] | 50.27 | 3.15 | 17.49 | | 14.77 | | |
| $C_2H_5$ | 4-F φ | 2 | CALCULATED | 61.79 | 5.18 | 18.01 | 8.14 | | | |
| | | | FOUND - m.p., other[b] | 60.37 | 5.16 | 18.03 | 8.07 | | | |
| $C_2H_5$ | 2-F φ | 2 | CALCULATED | 61.79 | 5.18 | 18.01 | 8.14 | | | |
| | | | FOUND - m.p., other[b] | 61.59 | 5.12 | 17.85 | 7.94 | | | |
| Cl | 3,4-$Cl_2$ φ | 7 | CALCULATED | 41.33 | 2.07 | 14.46 | | 36.31 | | |
| | | | FOUND - m.p., other[b] | 41.79 | 2.21 | 14.5 | | 32.59 | | |
| Cl | 3-$NO_2$ φ | 7 | CALCULATED | 45.04 | 2.64 | 21.01 | | | | |
| | | | FOUND - m.p., other[b] | 45.11 | 2.50 | 20.67 | | | | |
| Cl | α-naphthyl | 7 | CALCULATED | 61.88 | 3.71 | 15.46 | | 13.04 | | |
| | | | FOUND - m.p., other[b] | 61.08 | 3.76 | 15.18 | | 12.73 | | |
| $CH_2$ φ | φ | 1 | CALCULATED | 73.62 | 5.45 | 15.15 | | | | |
| | | | FOUND - m.p., other[b] | 73.34 | 5.45 | 15.17 | | | | |
| $CH_3CH_2CH_2$— | φ | 1 | CALCULATED | 68.09 | 6.59 | 18.33 | | | | |
| | | | FOUND - m.p., other[b] | 67.84 | 6.49 | 18.33 | | | | |
| $CH_2$=$CHCH_2$— | φ | 1 | CALCULATED | 68.70 | 5.76 | 18.49 | | | | |
| | | | FOUND - m.p., other[b] | 68.34 | 5.78 | 18.39 | | | | |
| Br | 2-pyrazine | 3 | CALCULATED | 35.84 | 2.26 | 26.13 | | | 29.81 | |
| | | | FOUND - m.p., other[b] | 35.24 | 2.33 | 26.18 | | | 29.09 | |
| I | 2-pyrazine | 5 | CALCULATED | 30.49 | 1.92 | 22.23 | | | | 40.28 |
| | | | FOUND - m.p., other[b] | 30.67 | 2.13 | 22.34 | | | | 40.39 |
| Cl | 2-pyrazine | 7 | CALCULATED | 42.96 | 2.70 | 31.32 | | 15.86 | | |
| | | | FOUND - m.p., other[b] | 43.10 | 2.90 | 31.41 | | 15.89 | | |
| I | 2-$CH_3O$ φ | 5 | CALCULATED | 38.50 | 2.94 | 12.25 | | | | 36.98 |
| | | | FOUND - m.p., other[b] - 280-281 | 39.09 | 3.77 | 12.81 | | | | 33.64 |
| Cl | 3,5-$(CH_3O)_2$ φ | 7 | CALCULATED | 51.16 | 4.29 | 14.91 | | 12.58 | | |
| | | | FOUND - m.p., other[b] | 51.35 | 4.18 | 14.78 | | 12.84 | | |
| Br | 3,5-$(CH_3O)_2$ φ | 3 | CALCULATED | 44.18 | 3.90 | 12.88 | | | 24.50 | |
| | | | FOUND - m.p., other[b] - 0.78% $H_2O$ | 43.81 | 3.74 | 13.08 | | | 24.57 | |
| I | 3,5-$(CH_3O)_2$ φ | 5 | CALCULATED | 38.62 | 3.24 | 11.26 | | | | 34.01 |
| | | | FOUND - m.p. other[b] - 0.48% $H_2O$ | 37.26 | 3.15 | 11.15 | | | | 34.74 |
| I | 3-$C_2H_5O$ φ | 5 | CALCULATED | 40.35 | 3.38 | 11.76 | | | | 35.53 |
| | | | FOUND - m.p., other[b] | 40.31 | 3.23 | 12.04 | | | | 32.22 |
| Cl | 3-$C_2H_5O$ φ | 7 | CALCULATED | 54.24 | 4.55 | 15.81 | | 13.34 | | |
| | | | FOUND - m.p., other[b] - 7.57% $H_2O$ | 49.77 | 4.65 | 14.52 | | 12.38 | | |
| Br | 3-n-$C_3H_7O$ φ | 3 | CALCULATED | 48.16 | 4.35 | 12.96 | | | 24.65 | |
| | | | FOUND - m.p., other[b] | 47.86 | 4.30 | 12.87 | | | 25.33 | |
| I | 3-n-$C_2H_7O$ φ | 5 | CALCULATED | 42.06 | 3.80 | 11.32 | | | | 34.19 |
| | | | FOUND - m.p., other[b] | 42.41 | 3.75 | 11.85 | | 33.50 | | |
| Cl | 3-n-$C_2H_7O$ φ | 7 | CALCULATED | 55.82 | 5.04 | 15.02 | | 12.68 | | |
| | | | FOUND - m.p., other[b] | 55.89 | 5.22 | 14.99 | | 12.64 | | |
| I | 3-$C_2H_5OC_2H_4O$ φ | 5 | CALCULATED | 41.90 | 4.02 | 10.47 | | | | 31.63 |
| | | | FOUND - m.p., other[b] | 40.58 | 3.96 | 10.73 | | | | 32.69 |

[a] In all of the samples where $X_1$ is halogen, the procedure number listed refers only to the appropriate halogenation procedure and presumes Procedure 1 or 2 has already been accomplished.
[b] A majority of the products exhibit melting points that are not necessarily a distinguishing characteristic of the compound either because of decomposition or greater than 200° and are therefore not listed.

EXAMPLE 12

2-Amino-6-(2-furyl)-4-pyrimidinol

To a 3-neck, 500 ml. flask fitted with a paddle stirrer, Dean-Stark trap, and a reflux condenser is added 5.76 g. of powdered guanidine carbonate (13.9 M), 200 ml. absolute $C_2H_5OH$ and 20 toluene. The solution is removed azeotropically. The reaction mixture is allowed to cool to 50° C., the Dean-Stark trap removed, and 10.4 g. (64 mM) of ethyl-2-furyl-acetate (57.07 mM) is added. The reaction mixture is heated at reflux for 18 hours; 50 ml. of water is added and heating is continued for 30 minutes. The reaction is allowed to cool to 25° C. Chips of carbon dioxide are added until the mixture is neutral and the flask is placed in the refrigerator at 5° C. under vacuum to yield 5.6 g. (49%) of pure 2-amino-6-(2-furyl)-4-pyrimidinol.

EXAMPLE 13

2-Amino-6-(m-chlorophenyl)-4-pyrimidinol

To a 3-neck, 500 ml. RB flask fitted with an overhead stirrer, condenser, and Dean-Stark trap under nitrogen is added 5.76 g. (32 mmole) of powdered guanidine carbonate, 200 ml. of absolute ethanol and 20 ml. of toluene. By heating to reflux 100 ml. of solvent is removed via the trap following which the solution is cooled to approximately 50° C. and trap removed. Ethyl-m-chlorobenzoyl acetate (14.8 g., 65 mmole) is introduced into the vessel and the reaction is stirred at reflux for 17 hours. Approximately 30 ml. of water is added and heating continued for 30 minutes. The mixture is then cooled in a refrigerator for 18 hours. The precipitate is filtered and washed with ethanol followed by ether and dried at 60° C. under vacuum to yield 10.6 g. (74%) of 2-amino-6-(m-chlorophenyl)-4-pyrimidinol.

EXAMPLE 14

2-Amino-6-(o-methoxyphenyl)-4-pyrimidinol

Following the procedure of Example 12 but substituting 5.67 g. (31.5 mM) of guanidine carbonate, 200 ml. of absolute ethanol, 20 ml. of toluene, 14.15 g. of ethyl-o-methoxybenzoyl acetete, and 150 hours of reflux gives 7.91 g. (57.8%) of 2-amino-6-(o-methoxypenyl)-4-pyrimidinol as a white solid (m.p. 283.5°–284.5° C.)

EXAMPLE 15

2-Amino-5-bromo-6-(m-chlorophenyl)-4-pyrimidinol

To 3.13 g. (15 mM) of 2-amino-6-(m-chlorophenyl)-4-pyrimidinol is added 80 ml. of glacial acetic acid. The solution is heated to 80° C. and 0.81 ml. of $Br_2$ is added. The mixture is allowed to stir at 80° C. for 15 minutes and cooled to 25° C. The mixture is evaporated to dryness under vacuum at 40° C. and the resulting solids heated at reflux with 150 ml. of water. The reaction mixture is cooled and filtered, and the solids washed very well with cold water. The solids are dried at 60° C. in a vacuum oven and pulverized when dry. The boiling water tritration is repeated. 3.90 G. (86.9%) of title compound is recovered. Recrystallization of the solids from water:DMF by adding DMF slowly to a stirring slurry of 3.9 g. of compound in 150 ml. boiling water until solution occurs, cooling and filtering yields analytically pure material (80% recovery).

EXAMPLE 16

2-Amino-6-(m-chlorophenyl)-5-iodo-4-pyrimidinol

To 3.13 g. (15 mM) of 2-amino-6-(m-chlorophenyl)-4-pyrimidinol is added 50 ml. water+0.80 g. sodium hydroxide (20 mM). The mixture is heatead to dissolve the pyrimidinol and filtered if necessary. It is cooled to 25° C. and 3.79 g. of $I_2$ (powdered) is added in 100 ml. chloroform. The excess $I_2$ is washed in with 30 ml. chloroform. The reaction mixture is allowed to stir vigorously with paddle stirrer at 25° C. for 4 hours.

The reaction is filtered and the solids washed very well with water until the aqueous wash is neutral to litmus. The solids are then washed with acetone until the acetone wash is colorless. (It is desirable to pulverize the solids before washing with acetone). Drying the solids at 60° C. yields 3.50 g. (67%) of 2-amino-6-(m-chlorophenyl)-4-pyrimidinol.

EXAMPLE 17

2-Amino-5-iodo-6-(2-furyl)-4-pyrimidinol

To 2.65 g. (15 mM) of 2-amino-6-(2-furyl-4-pyrimidinol is added 50 ml. water and 0.72 g. sodium hydroxide. The reaction mixture is heated to 75° C. to effect solution and then cooled to 25° C. A slurry of 4.0 g. (15.8 mM) of powdered iodine in 100 ml. chloroform is added, with vigorous stirring, and the reaction mixture is allowed to stir for 2 hours at ambient temperature. The reaction mixture is filtered. The solids are washed well with water (until wash is neutral to litmus) followed by acetone (until the acetone wash is colorless), and dried in a vacuum oven to give 3.95 g. (87%) of 2-amino-5-iodo-6-(2furyl)-4-pyrimidinol.

EXAMPLE 18

2-Amino-5-bromo-6-(2-furyl)-4-pyrimidinol

To 2.65 g. (15 mM) of 2-amino-6-(2-furyl)-4-pyrimidinol is added 50.0 ml. of water and 0.66 sodium hydroxide (16.5 mM). A cloudy solution results. The solution is allowed to stir for 30 minutes and 0.9 ml. $Br_2$ (2.62 g., 16.5 mM) in 20 ml. chloroform is added. The solution is allowed to stir vigorously for 2 hours and is filtered. The solids are washed well with water (until neutral to litmus) followed by acetone (until acetone is colorless) and dried at 60° C. to give 3.3 g. of 2-amino-5-bromo-6-(2-furyl)-4-pyrimidinol (86%).

EXAMPLE 19

2-Amino-5-chloro-6-phenyl-4-pyrimidinol

To 1.87 g. (10 mM) of 2-amino-6-pheny-4-pyrimidinol is added 50 ml. of glacial acetic acid and 1.46 g. (11 mM) of N-chlorosuccinimide. The mixture is heated with magnetic stirring under nitrogen at 90° C. for 2 hours (solution was complete in less than 20 minutes). The heat is removed and the amber solution is allowed to cool to room temperature. The solution is evaporated to a volume of 10 ml. under vacuum, cooled to 20° C. and filtered. The resulting solids are washed successively with $CH_3COOH$ (5 ml.), water (50 ml.), water (50 ml), acetone (100 ml.) and diethyl ether (100 ml.). The solids are dried at 60° C. in a vacuum oven to yield 1.40 g. (63%) of title compound. The solids can be recrystallized from ethanol:DMF by adding DMF to a hot, ethanol slurry of the pyrimidine until solution is complete. Cooling the solution at 5° C. for 18 hours filtering and drying gives analytically pure 2-amino-5-chloro-6-phenyl-4-pyrimidinol.

EXAMPLE 20

2- Amino-5-iodo-6-phenyl-4-pyrimidinol

Following the procedure of Example 16 but substituting 21.4 g. (0.113 M) of 2-amino-6-phenyl-4-pyrimidinol, 200 ml. water, 500 ml. chloroform, 5.6 g.

sodium hydroxide and 28.8 g. I$_2$, a yield of 29.0 g. (78%) of 2-amino-5-iodo-6-phenyl-4-pyrimidinol is obtained.

EXAMPLE 21

2-Amino-5-iodo-6-phenyl-4-pyrimidinol, zinc salt

To 1.56 g. (5 mmole) of 2-amino-5-iodo-6-phenyl-4-pyrimidinol in 15 ml. of methanol under nitrogen with stirring at room temperature is added 1.1 ml. of a 25% NaOCH$_3$/CH$_3$OH solution. After five minutes 340 mg. (2.5 mmole) of anhydrous zinc chloride (ZnCl$_2$) was added. After one hour the heterogeneous solution is concentrated to dryness, washed with 2×50 ml. water, filtered, and dried in vacuo at 60° C. for 18 hours. The product is a white solid with m.p. at 285° C.

The present invention comprises the administration of a compound of the formula:

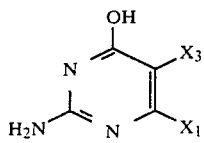

wherein X$_3$ is equal to X, X$_4$, or X$_5$ wherein X$_4$ is fluoro, chloro, bromo or iodo, and X$_5$ is mono-, di- or trihalomethyl, mono-, di- or trifluoroethyl, perfluoropropyl, and wherein X is alky of from 1 to 3 carbon atoms, inclusive, 2-propynyl and 2-propenyl, and X$_1$ is a member selected from the group consisting of (a) phenyl,
(b) a monosubstituted phenyl of the formula:

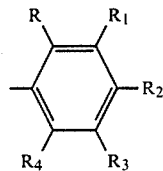

wherein one of the groups R, R$_1$, R$_2$, R$_3$, R$_4$ is not hydrogen and wherein R or R$_4$ is alkyl of from 1 to 8 carbon atoms, inclusive, alkoxy of from 1 to 8 carbon atoms, fluoro, chloro, bromo, iodo or nitro; R$_1$ or R$_3$ is fluoro, chloro, bromo, iodo, nitro; trifluoromethyl or alkoxy of from 1 to 8 carbon atoms, alkoxyethyloxy wherein alkoxy is from 1 to 3 carbon atoms, inclusive, or

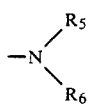

wherein R$_5$ and R$_6$ are the same or different and are alkyl of from 1 to 8 carbon atoms, inclusive, benzyl, or taken together with

are a saturated cycloalkylamino group

wherein n' is 3, 4, 5 or 6 or dialkyl substituted cycloalkylamino wherein each alkyl is from 1 to 3 carbon atoms, inclusive; and R$_2$ is chloro, fluoro, bromo, iodo, or alkyl of from 1 to 5 carbon atoms, inclusive;

(c) a disubstituted phenyl of the formula:

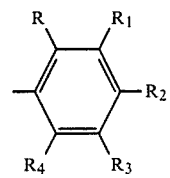

wherein any two of R, R$_1$, R$_2$, R$_3$ and R$_4$ are not hydrogen and are the same or different and are fluoro, chloro, bromo, iodo, alkyl of from 1 to 8 carbon atoms, alkoxy of from 1 to 8 carbon atoms, nitro and trifluoromethyl;

(d) a trihalo substituted phenyl wherein halo is chloro, bromo, iodo, or fluoro;

(e) α-naphthyl of the formula:

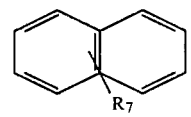

wherein R$_7$ is substituted in either ring and is hydrogen, alkyl of from 1 to 8 carbon atoms, inclusive, including isomeric forms, alkoxy of from 1 to 8 carbon atoms, inclusive, including isomeric forms, fluoro, chloro, iodo, bromo or nitro;

(f) 2-furyl,
(y) 3-pyridyl,
(h) 2-pyridyl and
(i) 2-pyrazyl, or a salt thereof in association with a pharmaceutical carrier to a human or animal.

Suitable pharmacologically acceptable acid addition salts are for example the hydrochloride, sulfate, phosphate, nitrate, and the like. These salts can be used in the same manner as the base compounds.

According to the present invention, the immunoregulatory system is altered by administering the active ingredients to a suitable host. By "host" is meant animals, i.e., intact viable animals. The host may be warm-blooded animals such as mammals, e.g., mice, rats, rabbits, bovines, pigs, hamsters, dogs, cats, guinea pigs, horses, goats, sheep, monkeys, man; and birds, e.g., chickens, ducks, turkeys, pigeons, parakeets, and canaries. The mode of administration can be parenterally such as subcutaneously, intramuscularly, intradermally, intraperitoneally, intrathecally, intravenously or locally, on a mucous membrane such as intranasally, pharyngolaryngeally, bronchially, broncholialy, intravaginally, rectally or ocularly. The mode of administration can also be by implantation. Alternatively or concurrently, administration can be by the oral route, a preferred mode of administration. Practically, it is advantageous to administer the active ingredient to the host orally, intranasally, topically, locally, subcutaneously or intramuscularly.

Preferred compounds are:
2-amino-5-iodo-6-(3-bromophenyl)-4-pyrimidinol;
2-amino-5-bromo-6-(3-fluorophenyl)-4-pyrimidinol;
2-amino-5-bromo-6-(3-ethoxyethylphenyl)-4-pyrimidinol;
2-amino-5-bromo-6-(2-methoxyphenyl)-4-pyrimidinol;
2-amino-5-chloro-6-(2-methoxyphenyl)-4-pyrimidinol;
2-amino-5-iodo-6-(2-methoxyphenyl)-4-pyrimidinol;
2-amino-5-bromo-6-(3-chlorophenyl)-4-pyrimidinol;
2-amino-5-iodo-6-(3-chlorophenyl)-4-pyrimidinol;
2-amino-5-chloro-6-(3-chlorophenyl)-4-pyrimidinol;
2-amino-5-chloro-6-(2-fluorophenyl)-4-pyrimidinol;
2-amino-5-chloro-6-(3-fluorophenyl)-4-pyrimidinol;
2-amino-5-bromo-6-(2-fluorophenyl)-4-pyrimidinol;
2-amino-5-iodo-6-(3-fluorophenyl)-4-pyrimidinol;
2-amino-5-iodo-6-phenyl-4-pyrimidinol;
2-amino-5-chloro-6-phenyl-4-pyrimidinol;
2-amino-5-bromo-6-phenyl-4-pyrimidinol;
2-amino-5-chloro-6-(3-methoxyphenyl)-4-pyrimidinol;
2-amino-5-bromo-6-(3-methoxyphenyl)-4-pyrimidinol;
2-amino-5-iodo-6-(3-methoxyphenyl)-4-pyrimidinol;
2-amino-5-bromo-6-(2-pyridyl)-4-pyrimidinol;
2-amino-5-iodo-6-(3,4-dichlorophenyl)-4-pyrimidinol;
2-amino-5-bromo-6-(α-naphthyl)-4-pyrimidinol;
2-amino-5-chloro-6-(3-nitrophenyl)-4-pyrimidinol;
2-amino-5-iodo-6-(3-nitrophenyl)-4-pyrimidinol;
2-amino-5-iodo-6-(3-trifluoromethylphenyl)-4-pyrimidinol;
2-amino-5-ethyl-6-phenyl-4-pyrimidinol;
2-amino-5-bromo-6-(3,5-dimethoxyphenyl)-4-pyrimidinol;
2-amino-5-chloro-6-(3-propyloxyphenyl)-4-pyrimidinol;
or the pharmaceutically acceptable acid addition salts or alkali metal or alkaline earth metal salts thereof.

The method of the present invention is for alteration of the immunoregulatory system of the host animal. The administration of the active compounds can be used to treat acquired or congenital hypogammaglobulinemia.

The dosage administered will be dependent upon the the type of animal involved, its age, health, weight, kind of concurrent treatment, if any, frequency of treatment, therapeutic ratio, and tolerance.

Illustratively, dosage levels of the administered active ingredients can be: intravenous, 0.1 to about 100 mg./kg.; intraperitoneal, 0.1 to about 100 mg./kg.; subcutaneous, 0.1 to about 150 mg./kg.; intramuscular, 0.1 to about 150 mg./kg.; orally, 0.1 to about 400 mg./kg., and preferably about 1 to 10 mg./kg.; intranasal instillation, 0.1 to about 50 mg./kg.; and aerosol, 0.1 to about 50 mg./kg. of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.1 to about 50% w/w of the composition; preferably about 1 to about 20% w/w of the composition; and for parenteral use in a concentration of from about 0.5 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelating solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred or by dry powder for insufflation.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like non-toxic, orally acceptable pharmaceutical diluents. The prepared premix is then conveniently added to the regular feed.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as co-solvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated mutliples of any of the foregoing, and other forms as herein described.

The active ingredients to be employed for immunoregulation can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

EXAMPLE 22

Hard-Gelatin Capsules

One thousand two-piece hard gelatin capsules for oral use, each capsule containing 100 mg. of 2-amino-5-bromo-6-phenyl-4(1H)-pyrimidinone, are prepared from the following types and amounts of ingredients:

2-Amino-5-bromo-6-phenyl-4(1H)-pyrimidinone, micronized: 100 gm.
Lactose: 100 gm.
Corn starch: 20 gm.
Talc: 20 gm.
Magnesium stearate: 2 gm.

The 2-amino-5-bromo-6-phenyl-4(1H)-pyrimidinone, finely divided by means of an air micronizer, is added to the other finely powdered ingredients, mixed thoroughly and then encapsulated in the usual manner.

The foregoing capsules are useful for preventing or treating skin graft rejection by the oral administration of one or two capsules one to four times a day.

Using the procedure above, capsules are similarly prepared containing 2-amino-5-bromo-6-phenyl-4(1H)-pyrimidinone in 50, 250 and 500 mg. amounts by substituting 50 gm., 250 gm. and 500 gm. of 2-amino-5-bromo-6-phenyl-4(1H)-pyrimidinone for the 100 gm. used above.

EXAMPLE 23

Soft Gelatin Capsules

One-piece soft gelatin capsules for oral use, each containing 250 mg. of 2-amino-5-bromo-6-phenyl-4(1H)-pyrimidinone (finely divided by means of an air micronizer), are prepared by first suspending the compound in 0.5 ml. of corn oil to render the material capsulatable and then capsulating in the above manner.

EXAMPLE 24

Tablets

One thousand tablets, each containing 500 mg. of 2-amino-5-bromo-6-phenyl-4(1H)-pyrimidinone, are prepared from the following types and amounts of ingredients:

2-Amino-5-bromo-6-phenyl-4(1H)-pyrimidinone: 500 gm.
Lactose: 75 gm.
Corn starch: 50 gm.
Magnesium stearate: 4 gm.
Light liquid petrolatum micronized: 5 gm.

The 2-amino-5-bromo-6-phenyl-4(1H)-pyrimidinone, finely divided by means of an air micronizer, is added to the other ingredients and then thoroughly mixed and slugged. The slugs are broken down by forcing through a Number Sixteen screen. The resulting granules are then compressed into tablets, each tablet containing 500 mg. of 2-amino-5-bromo-6-phenyl-4(1H)-pyrimidinone.

The foregoing tablets are useful for treating hypogammaglobulinemia by the oral administration of one or two tablets one to four times a day.

Using the procedure above, tablets are similarly prepared containing 2-amino-5-bromo-6-phenyl-4(1H)-pyrimidinone in 250 mg. and 100 mg. amounts by substituting 250 gm. and 10 gm. of 2-amino-5-bromo-6-phenyl-4(1H)-pyrimidinone for the 500 gm. used above.

EXAMPLE 25

Oral Suspension

One thousand ml. of an aqueous suspension for oral use, containing in each teaspoonful (5 ml.) dose, 500 mg. of 2-amino-5-bromo-6-phenyl-4-(1H)-pyrimidinone, is prepared from the following types and amounts of ingredients:

2-Amino-5-bromo-6-phenyl-4(1H)-pyrimidinone, micronized: 100 gm.
Citric acid: 2 gm.
Benzoic acid: 1 gm.
Sucrose: 700 gm.
Tragacanth: 5 gm.
Lemon oil: 2 gm.
Deionized water, q.s. 1000 ml.

The citric acid, benzoic acid, sucrose, tragacanth and lemon oil are dispersed in sufficient water to make 850 ml. of suspension. The 2-amino-5-bromo-6-phenyl-4(1H)-pyrimidinone, finely divided by means of an air micronizer, is stirred into the syrup until uniformly distributed. Sufficient water is added to make 1000 ml.

EXAMPLE 26

A sterile aqueous suspension for parenteral injection, containing in 1 ml. 300 mg. of 2-amino-5-iodo-6-phenyl-4(1H)-pyrimidinone, is prepared from the following types and amounts of ingredients:

2-Amino-5-iodo-6-phenyl-4(1H)-pyrimidinone, micronized: 300 gm.
Polysorbate 80: 5 gm.
Methylparaben:2.5 gm.
Propylparaben:0.17 gm.
Water for injection, q.s. 1000 ml.

All the ingredients, except the 2-amino-5-iodo-6-phenyl-4(1H)-pyrimidinone, are dissolved in the water and the solution sterilized by filtration. To the sterile solutuion is added the sterilized 2-amino-5-iodo-6-phenyl-4(1H)-pyrimidinone, finely divided by means of an air micronizer, and the final suspension is filled into sterile vials and the vials sealed.

The composition so prepared is useful for treating agammaglobinemia at a dose of 1 milliliter (IM) three times a day.

EXAMPLE 27

Suppository, Rectal and Vaginal

One thousand suppositories, each weighing 2.5 gm. and containing 150 mg. of 2-amino-5-bromo-6-phenyl-4(2 IH)-pyrimidinone are prepared from the following types and amounts of ingredients:

2-Amino-5-bromo-6-phenyl-4(1H)-pyrimidinone, micronized:150 gm.
Propylene glycol:150 gm.
Polyethylene glycol, 4000 q.s.:2,500 gm.

The 2-amino-5-bromo-6-phenyl-4(1H)-pyrimidinone is finely divided by means of an air micronizer and added to the propylene glycol and the mixture passed through a colloid mill until uniformly dispersed. The polyethylene glycol 40,000 is melted and the propylene glycol dispersion added slowly with stirring. The suspension is poured into unchilled molds at 40° C. The composition is allowed to cool and solidify and then removed from the mold and each suppository foil wrapped.

EXAMPLE 28

Intranasal Suspension

One thousand ml. of a sterile aqueous suspension for intranasal instillation, containing in each ml. 150 mg. of 2-amino-5-bromo-6-phenyl-4(1H)-pyrimidinone, is prepared from the following types and amounts of ingredients.

2-Amino-5-bromo-6-phenyl-4(1H)-pyrimidinone, micronized:150 gm.
Polysorbate 80:5 gm.
Methylparaben:2.5 gm.
Propylparaben:0.17 gm.
Deionized water, q.s. 1000 ml.

All the ingredients, except the 2-amino-5-bromo-6-phenyl-4(1H)-pyrimidinone, are dissolved in the water and the solution sterilized by filtration. To the sterile solution is added the sterilized 2-amino-5-bromo-6-phenyl-4(1H)-pyrimidinone, finely divided by means of an air micronizer, and the final suspension is aseptically filled into sterile containers.

EXAMPLE 29

Animal Feed

One thousand grams of feed premix is prepared from the following types and amounts of ingredients:

2-Amino-5-bromo-6-phenyl-4(1H)-pyrimidinone:20 gm.
Soybean meal:400 gm.
Fish meal:400 gm.
Wheat germ oil:50 gm.
Sorghum molasses:130 gm.

The ingredients are mixed together and pressed into pellets.

For larger animals the premix can be added to the animal's regular feed in an amount calculated to give the desired dose of 2-amino-5-bromo-6-phenyl-4(1H)-pyrimidinone. For example, one part of premix is added to 2.5 parts of a cat's regular feed to provide the desired dose of 200 mg./kg./day for a cat of 2.5 kg.

An active ingredient can also be present, as shown in Examples 30-33 in the undiluted pure form for use locally about the cutis, intranasally, pharyngolaryngeally, bronchially, broncholially or orally.

EXAMPLE 30

Oral Powder

One thousand grams of 2-amino-5-bromo-6-phenyl-4(1H)-pyrimidinone in bulk form is finely divided by means of an air micronizer. The micronized powder is divided into individual doses of 250 mg. and packaged.

EXAMPLE 31

Hard Gelatin Capsules

One thousand two-piece hard gelatin capsules for oral use, each capsule containing 100 mg. of 2-amino-5-bromo-6-phenyl-4(1H)-pyrimidinone, are prepared from 100 grams of 2-amino-5-bromo-6-phenyl-4(1H)-pyrimidinone.

The 2-amino-5-bromo-6-phenyl-4(1H)-pyrimidinone is finely divided by means of an air micronizer and encapsulated in the usual manner.

Using the procedure above, capsules are similarly prepared containing 2-amino-5-bromo-6-phenyl-4(1H)-pyrimidinone in 50, 250 and 500 mg. amounts by substituting 50 gm., 250 gm. and 500 gm. of 2-amino-5-bromo-6-phenyl-4(1H)-pyrimidinone for the 100 gm. used above.

EXAMPLE 32

Following the procedure of the preceding Examples 22 through 31, inclusive, compositions are prepared substituting equivalent amounts of the pharmaceutically acceptable acid addition salts of 2-amino-5-bromo-6-phenyl-4(1H)-pyrimidinone for the free base of the examples.

EXAMPLE 33

Following the procedure of the preceding Examples 22 through 31, inclusive, compositions are prepared substituting equivalent amounts of
2-amino-5-iodo-6-(3-bromophenyl)-4-pyrimidinol;
2-amino-5-bromo-6-(3-fluorophenyl)-4-pyrimidinol;
2-amino-5-bromo-6-(3-ethoxyethylphenyl)-4-pyrimidinol;
2-amino-5-bromo-6-(2-methoxyphenyl)-4-pyrimidinol;
2-amino-5-chloro-6-(2-methoxyphenyl)-4-pyrimidinol;

2-amino-5-iodo-6-(2-methoxyphenyl)-4-pyrimidinol;
2-amino-5-bromo-6-(3-chlorophenyl)-4-pyrimidinol;
2-amino-5-iodo-6-(3-chlorophenyl)-4-pyrimidinol;
2-amino-5-chloro-6-(3-chlorophenyl)-4-pyrimidinol;
2-amino-5-chloro-6-(2-fluorophenyl)-4-pyrimidinol;
2-amino-5-chloro-6-(3-fluorophenyl)-4-pyrimidinol;
2-amino-5-bromo-6-(2-fluorophenyl)-4-pyrimidinol;
2-amino-5-iodo-6-(3-fluorophenyl)-4-pyrimidinol;
2-amino-5-iodo-6-phenyl-4-pyrimidinol;
2-amino-5-chloro-6-phenyl-4-pyrimidinol;
2-amino-5-bromo-6-phenyl-4-pyrimidinol;
2-amino-5-chloro-6-(3-methoxyphenyl)-4-pyrimidinol;
2-amino-5-bromo-6-(3-methoxyphenyl)-4-pyrimidinol;
2-amino-5-iodo-6-(3-methoxyphenyl)-4-pyrimidinol;
2-amino-5-bromo-6-(2-pyridyl)-4-pyrimidinol;
2-amino-5-iodo-6-(3,4-dichlorophenyl)-4-pyrimidinol;
2-amino-5-bromo-6-(α-naphthyl)-4-pyrimidinol;
2-amino-5-chloro-6-(3-nitrophenyl)-4-pyrimidinol;
2-amino-5-iodo-6-(3-nitrophenyl)-4-pyrimidinol;
2-amino-5-iodo-6-(3-trifluoromethylphenyl)-4-pyrimidinol;
2-amino-5-ethyl-6-phenyl-4-pyrimidinol;
2-amino-5-bromo-6-(3,5-dimethoxyphenyl)-4-pyrimidinol;
2-amino-5-chloro-6-(3-propyloxyphenyl)-4-pyrimidinol;
or the pharmaceutically acceptable acid addition salts or the alkali metal or alkaline earth metal salts of each of the foregoing compounds for active ingredients of each of the examples as described above and in Examples 22 through 31, inclusive.

We claim:

1. A process for treating an animal or human having acquired or congenital hypogammaglobulinemia, acquired or congenital agammaglobulinemia, comprising the systemic administration of an effective amount for treating said diseases of a compound of the formula:

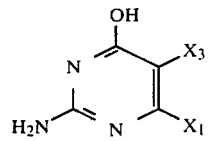

wherein $X_3$ is equal to X, $X_4$, or $X_5$ wherein $X_4$ is fluoro, chloro, bromo or iodo, and $X_5$ is mono-, di- or trihalo methyl, mono-, di- or trifluoroethyl, perfluoropropyl and X is alkyl of from 1 to 3 carbon atoms, inclusive, 2-propynyl, 2-propenyl, and alkyloxyacyl where alkyl is as defined above, and $X_1$ is a member selected from the group consisting of:

(a) phenyl,
(b) a monosubstituted phenyl of the formula:

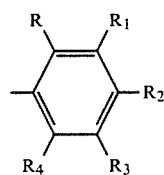

wherein provided that only one of groups R, $R_1$, $R_2$, $R_3$, $R_4$ is other than hydrogen and R or $R_4$ is alkyl of from 1 to 8 carbon atoms, inclusive, including isomeric forms, alkoxy of from 1 to 8 carbon atoms, inclusive, including isomeric forms, fluoro, chloro, bromo, iodo, or nitro; $R_1$ or $R_3$ is fluoro, chloro, bromo, iodo, nitro, trifluoromethyl or alkoxy of from one to eight carbon atoms, alkoxyethyloxy wherein alkoxy is from 1 to 5 carbon atoms, inclusive, or

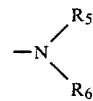

wherein $R_5$ and $R_6$ are the same or different and are alkyl of from 1 to 8 carbon atoms, inclusive, benzyl or taken together with

are a saturated cycloalkylamino group

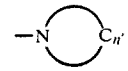

wherein n' is 3, 4, 5 or 6 or dialkyl substituted cycloalkylamino wherein each alkyl is from 1 to 3 carbon atoms, inclusive; and $R_2$ is chloro, fluoro, bromo, iodo, or alkyl of from 1 to 3 carbon atoms, inclusive.

(c) a disubstituted phenyl of the formula:

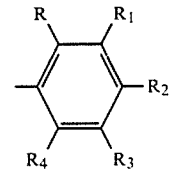

wherein any two of R, $R_1$, $R_2$, $R_3$ and $R_4$ are not hydrogen and are the same or different and are fluoro, chloro, bromo, iodo, alkyl of from 1 to 8 carbon atoms, including isomeric forms, alkoxy of from 1 to 8 carbon atoms, inclusive isomeric forms, nitro and trifluoromethyl;

(d) a trihalo substituted phenyl wherein halo is chloro, bromo, iodo or fluoro, (e) α-naphthyl of the formula:

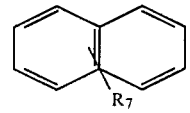

wherein R is substituted in either ring and is hydrogen, alkyl of from 1 to 8 carbon atoms, inclusive, including isomeric forms, alkoxy of from 1 to 8 carbon atoms, inclusive, including isomeric forms, fluoro, chloro, iodo, bromo or nitro, (f) 2-furyl,
(g) 3-pyridyl,
(h) 2-pyridyl and
(i) 2-pyrazyl, or a salt thereof in association with a pharmaceutical carrier to said human or animal.

2. The process of claim 1 wherein the amount of compound administered is from about 0.1 to about 10 mg/kg of body weight of the human or animal.

3. The process of claim 2 wherein the compound administered is 2-amino-5-bromo-6-phenyl-4(1H)-pyrimidinone.

4. The process of claim 2 wherein the compound administered is 2-amino-5-iodo-6-phenyl-4(1H)-pyrimidinone.

* * * * *

UNITED STATES PATENT OFFICE
CERTIFICATE OF CORRECTION

Patent No. 4,543,248        Dated  24 September 1985

Inventor(s)  Dale E. Stringfellow and Patricia E. Fast

It is certified that error appears in the above-identified patent and that said Letters Patent are hereby corrected as shown below:

Column 1, line 34: "5aminomethyl" should read: -- 5-aminomethyl --.
Column 2, line 67: "a the" should read: -- at the --.
Column 3, line 14: "cyromatography" should read: -- chromatography --.
Column 3, line 37: "nydrochloric" should read: -- hydrochloric --.
Column 3, line 62: "OCHhd 2)," should read: -- OCH$_2$), --.
Column 5, line 31: "o" should read: -- of --.
Column 6, line 10: "IN" should read: -- in --.
Column 6, lines 50-51: "pyrimidinols or pyrimidinols or pyrimidinones" should read: -- pyrimidinols or pyrimidinones --.
Column 6, line 53: "-6m-" should read: -- -6-m- --.
Column 6, line 58: "βketo" should read: -- β-keto --.
Column 9, line 7: "occures" should read: -- occurs --.
Column 10, line 36: "X$_3$32=CH$_2$OH" should read: -- X$_3$=CH$_2$OH --.
Column 9, Table heading: "X$_0$" should read: -- X$_3$ --.
Column 11 (Table) line 50: "αnaphthyl" should read : -- α-naphthyl --.
Column 13, Table heading: "X$_0$" should read: -- X$_3$ --.
Column 14, line 30 (Col. Br): "16.59" should read: -- 26.59 --.
Column 14, line 33 (Col. Br): "45.54" should read: -- 45.51 --.
Column 15, Table heading: "X$_0$" should read: -- X$_3$ --.
Column 17, line 43: "methoxypenyl" should read: -- methoxyphenyl --.

UNITED STATES PATENT OFFICE
CERTIFICATE OF CORRECTION

Patent No. 4,543,248            Dated  24 September 1985

Inventor(s)  Dale E. Stringfellow and Patricia E. Fast

It is certified that error appears in the above-identified patent and that said Letters Patent are hereby corrected as shown below:

Column 18, line 1: "heatead" should read: -- heated --.

Column 18, line 28: "(2furyl)" should read: -- (2-furyl) --.

Column 18, line 54: "water (50 ml.), water (50 ml)," should read: -- water (50 ml.), --.

Column 21, lines 40-41: "the the" should read: -- the --.

Signed and Sealed this

Twenty-first Day of October, 1986

[SEAL]

Attest:

DONALD J. QUIGG

Attesting Officer        Commissioner of Patents and Trademarks